(12) United States Patent
Musha et al.

(10) Patent No.: US 7,734,337 B2
(45) Date of Patent: Jun. 8, 2010

(54) APPARATUS FOR MEASURING BRAIN LOCAL ACTIVITY

(75) Inventors: Toshimitsu Musha, Yokohama (JP); Haruyasu Matsuzaki, Edogawa (JP)

(73) Assignee: Brain Functions Laboratory, Inc., Yokohama (JP)

( * ) Notice: Subject to any disclaimer, the term of this patent is extended or adjusted under 35 U.S.C. 154(b) by 75 days.

(21) Appl. No.: 12/073,462

(22) Filed: Mar. 5, 2008

(65) Prior Publication Data

US 2009/0105603 A1 Apr. 23, 2009

(30) Foreign Application Priority Data

Oct. 18, 2007 (JP) ............................. 2007-271544

(51) Int. Cl.
*A61B 5/04* (2006.01)
(52) U.S. Cl. ....................................... 600/544; 600/545
(58) Field of Classification Search ................. 600/544, 600/545, 409
See application file for complete search history.

(56) References Cited

U.S. PATENT DOCUMENTS

| | | | | |
|---|---|---|---|---|
| 5,083,571 A | * | 1/1992 | Prichep | ........................ 600/544 |
| 5,230,346 A | * | 7/1993 | Leuchter et al. | ............. 600/544 |
| 5,458,117 A | | 10/1995 | Chamoun et al. | |
| 5,611,350 A | * | 3/1997 | John | ........................... 600/378 |

| | | | | |
|---|---|---|---|---|
| 2004/0171960 A1 | * | 9/2004 | Musha et al. | ................ 600/544 |

FOREIGN PATENT DOCUMENTS

JP 3581361 7/2004

OTHER PUBLICATIONS

Musha T et al "EEG Z-score pattern matching diagnosis of AD" Alzheimer's Dementia: The Journal of the Alzheimer'S Association, Elsevier, New York, NY, US, vol. 1, No. 1, Jul. 1, 2005 p. 525.
Bennys K et al "Diagnostic value of quantitative EEG in Alzheimer's disease" Neurophysiologie Clinique, vol. 31, No. 3, Jun. 2001, pp. 153-160.

(Continued)

*Primary Examiner*—Robert L Nasser
*Assistant Examiner*—Michael D'Angelo
(74) *Attorney, Agent, or Firm*—Staas & Halsey LLP (57) ABSTRACT

For measuring a brain local activity, a predetermined frequency bandwidth wider than a frequency bandwidth of alpha waves of scalp potentials is divided into a predetermined number of frequency banks each having a fixed frequency width, data of each divided frequency bank is divided into segments of a predetermined duration on a time axis, a Z-score of the subject is determined from a first mean value of normalized power variances determined for the segments and a second mean value of normalized power variances predetermined in the same manner as the first mean value for a predetermined normal person group and a standard deviation of the normalized power variances in the group, and a mean value of the Z-scores determined over all of the frequency banks is mapped on a brain surface for each sensor, whereby a template of a specified brain disorder and likelihood of a subject to a specified brain disorder are calculated.

6 Claims, 7 Drawing Sheets

OTHER PUBLICATIONS

Jelic V et al "Quantitative electroencephalography in mild cognitive impairment: longitudinal changes and possible prediction of Alzheimer's disease" Neurobiology of Aging, vol. 21, 2000, pp. 533-540.

Musha T et al "Localization of impaired cortical neurons by EEG power fluctuation analysis" International Congress Series, vol. 1270, 2004, pp. 20-25.

Musha T, Matsuzaki H, Tsuboi M "Dynamic on-the-brain mapping of neuronal imparment" Neurodegenerative Diseases, vol. 4, No. suppl.1, May 2007, p. 343.

European Search Report issued on Feb. 25, 2009 in corresponding European Patent Application 08011953.0.

* cited by examiner

FIG.6C (○ ; mAD TEMPLATE, × ; sAD TEMPLATE, FIGURE IN CIRCLE INDICATES SUBJECT NO.)

FIG.7

APPARATUS FOR MEASURING BRAIN LOCAL ACTIVITY

BACKGROUND OF THE INVENTION

1. Field of the Invention

The present invention relates to an apparatus for measuring a brain local activity, and in particular to an apparatus for measuring or estimating a degree of neuronal impairment (diminishment) state in brain cortex such as a senile dementia disorder.

2. Description of the Related Art

With respect to senile dementia, it is statistically said that about 30% of nonagenarians are in dementia. This senile dementia is becoming a serious problem for the coming aging society.

Accordingly, such a dementia disorder should be preferably found as early as possible and treated before it results in a serious state. As an apparatus for measuring (estimating) a degree of the dementia disorder, an apparatus for measuring a brain local activity has been already proposed comprising: a plurality of sensors mounted on a head of a subject for measuring scalp potentials or magnetic fields of the subject; a computing unit for converting alpha wave components of output signals of the sensors into numerical data to determine a dipolarity at each sampling, for determining mean values of squared errors, within a fixed time interval, between a scalp potential or a magnetic field by an equivalent dipole at a dipolarity peak emergence time and the measured scalp potentials or magnetic fields or variances of the squared errors from the mean values for the sensors, and for mapping a contour concerning a distribution of the mean values or the variances on a scalp or a brain surface corresponding thereto; and an output unit for outputting a contour map (see e.g. patent document 1).

[Patent document 1] Japanese patent No. 3581361

The above-mentioned patent document 1 detects a functional impairment of neurons in some part of a brain by analyzing a scalp potential distribution of alpha waves, so that there have been following problems:

a) A large number of persons do not show alpha waves
b) The alpha waves are restrained in an eye-opening state, which is extremely unstable;
c) The alpha waves are highly affected by a state of mind;
d) Localization of a brain functional impairment degree only by the alpha waves does not properly coincide with a cerebral blood flow diminished part by SPECT (Single Photon Emission Computing Tomography).

Namely, since the patent document 1 consistently carries out a measurement based on the alpha waves, there have been problems that a functional impairment part of neurons can not be detected, a type and a degree of a brain disorder are unclear, and a part in which the neuronal function has recovered by various treatments is unclear.

SUMMARY OF THE INVENTION

It is accordingly an object of the present invention to provide an apparatus for measuring a brain local activity by which a type and a degree of a brain disorder, and a part of a head where a neuronal function has been impaired or recovered can be specified without restrictions of alpha waves.

In order to achieve the above-mentioned object, the inventors of this patent application have discovered that when a neuronal function in brain cortex is impaired, neuronal activities become unstable. This influence emerges as a fluctuation of a local brain wave power (T. Musha, T. Asada, F. Yamashita, T. Kinoshita, H. Matsuda, M. Uno, Z. Chen and W. R. Shankle, "A new EEG method for estimating cortical neuronal impairment that is sensitive to early stage Alzheimer's disease," Clinical Neurophysiology, 113 (2002) 1052-1058). It has been confirmed that this characteristic ranges over not only the alpha waves but also the entire area of frequencies (e.g. 2-40 Hz) of brain waves wider than the alpha waves.

Therefore, an apparatus for measuring a brain local activity according to the present invention comprises: a plurality of sensors mounted on a head of a subject for measuring scalp potentials of the subject; and a computing unit dividing a predetermined frequency bandwidth wider than a frequency bandwidth of alpha waves of the scalp potentials outputted from the sensors into a predetermined number of frequency banks each having a fixed frequency bandwidth, dividing data of each divided frequency bank into segments of a predetermined duration on a time axis, determining a Z-score of the subject from a first mean value of normalized power variances (hereinafter NPV) determined for the segments and a second mean value of normalized power variances predetermined in the same manner as the first mean value for a predetermined normal person group and a standard deviation of the normalized power variances in the group, and mapping on a brain surface for each sensor a mean value of the Z-scores determined over all of the frequency banks. Thus, the map of the local neuronal function impairment is prepared.

Since this map indicates how far a neuronal activity of a subject deviates from that of a normal person, namely "abnormality" of the neuronal activity, a Z-score of the subject is calculated. There are two types of abnormality, in which if "Z-score>0", it indicates that the fluctuation of the neuronal activity is larger than that of a normal person group, that is "unstable" while if "Z-score<0", it indicates that the neuronal activity is "inactive" as compared with that of the normal person group.

Also, an averaged analogous Z-score map is prepared for a group of a brain disease patient such as an Alzheimer's patient. This is made a template indicating a characteristic of the disease. By determining a cross-correlation coefficient between the Z-score of an individual subject and the template, the likelihood (similarity) therebetween can be indicated numerically.

For example, the above-mentioned fixed frequency bandwidth is 1 Hz, the predetermined number is 38, and the predetermined duration is 2.56 seconds.

Also, the above-mentioned sensors may be set in a terminal device, the computing unit may be set in a calculation center, and the terminal device and the calculation center may be connected through a communication line.

Furthermore, the present invention can provide a computer program for making a computer execute the steps of: dividing a predetermined frequency bandwidth wider than a frequency bandwidth of alpha waves of the scalp potentials measured by a plurality of sensors mounted on a head of a subject into a predetermined number of frequency banks each having a fixed frequency bandwidth, dividing data of each divided frequency bank into segments of a predetermined duration on a time axis, determining a Z-score of the subject from a first mean value of normalized power variances determined for the segments and a second mean value of normalized power variances predetermined in the same manner as the first mean value for a predetermined normal person group and a standard deviation of the normalized power variances in the group, and mapping on a brain surface for each sensor a mean value of the Z-scores determined over all of the frequency banks.

The above-mentioned program can further make a computer execute the steps of determining Z-scores of a patient group of a specific brain disease with respect to the predetermined normal person group, and determining a cross-correlation coefficient as a similarity to the Z-score of the subject with the Z-score of the patient group being made a template.

Furthermore, the present invention can provide a computer readable recording medium for recording the above-mentioned program.

As the present invention deals with entire brain waves from 2 Hz to 40 Hz permitting a brain waveform to be measured, such an enlargement of frequency area is essentially important, enabling the present invention to be applied regardless of a condition of closed eyes or opened eyes.

Furthermore, if standard templates concerning various brain diseases are experimentally prepared, a differential (discrimination) diagnosis concerning the diseases can be performed. Moreover, details of treatment effects for respective brain diseases can also be recognized from the change of the map.

BRIEF DESCRIPTION OF THE DRAWINGS

The above and other objects and advantages of the invention will be apparent upon consideration of the following detailed description, taken in conjunction with the accompanying drawings, in which the reference numerals refer to like parts throughout and in which.

DESCRIPTION OF THE EMBODIMENTS

Figure 1:
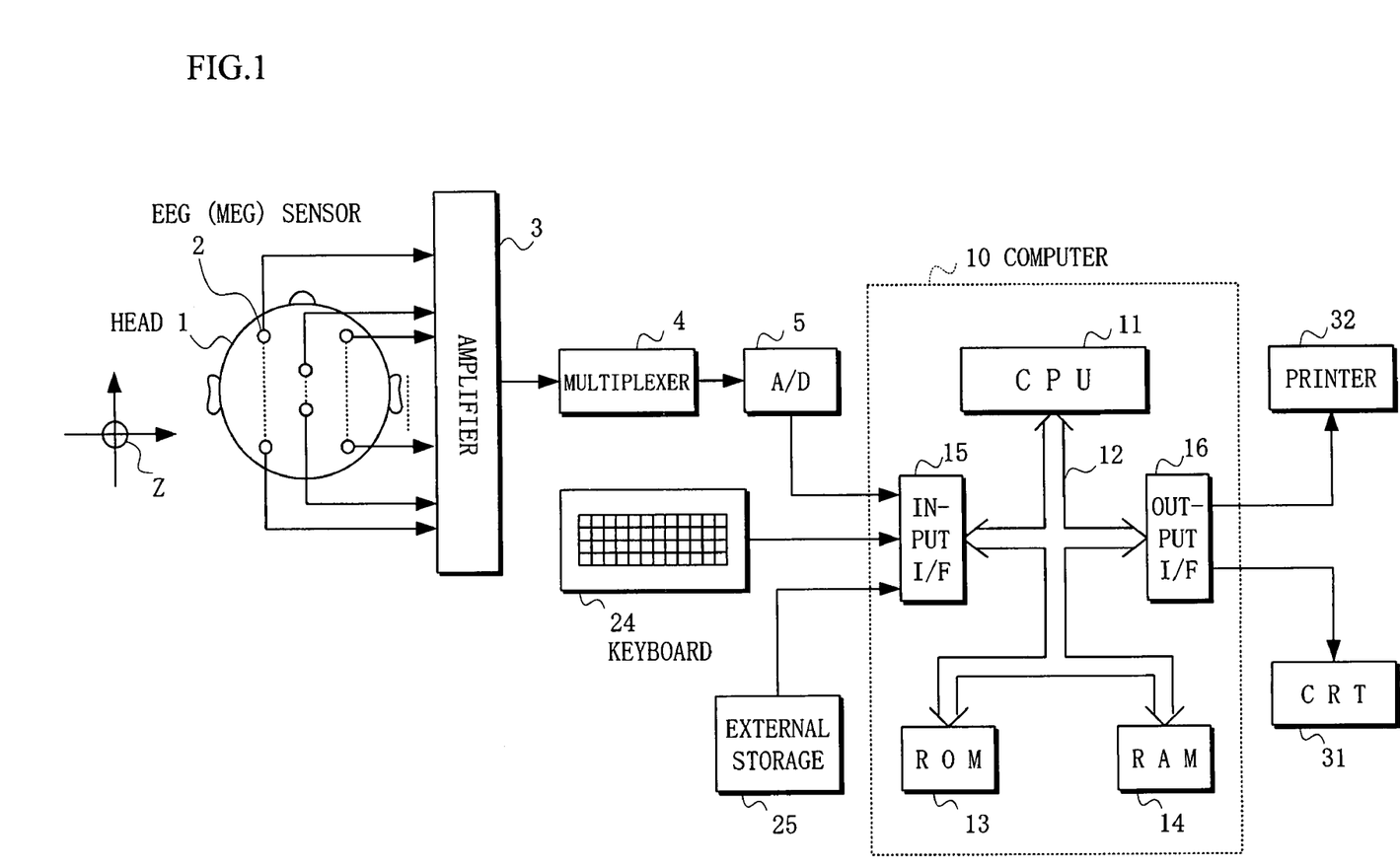
FIG. 1 is a block diagram showing an arrangement [1] of an apparatus for measuring a brain local activity according to the present invention.
Figure 2:
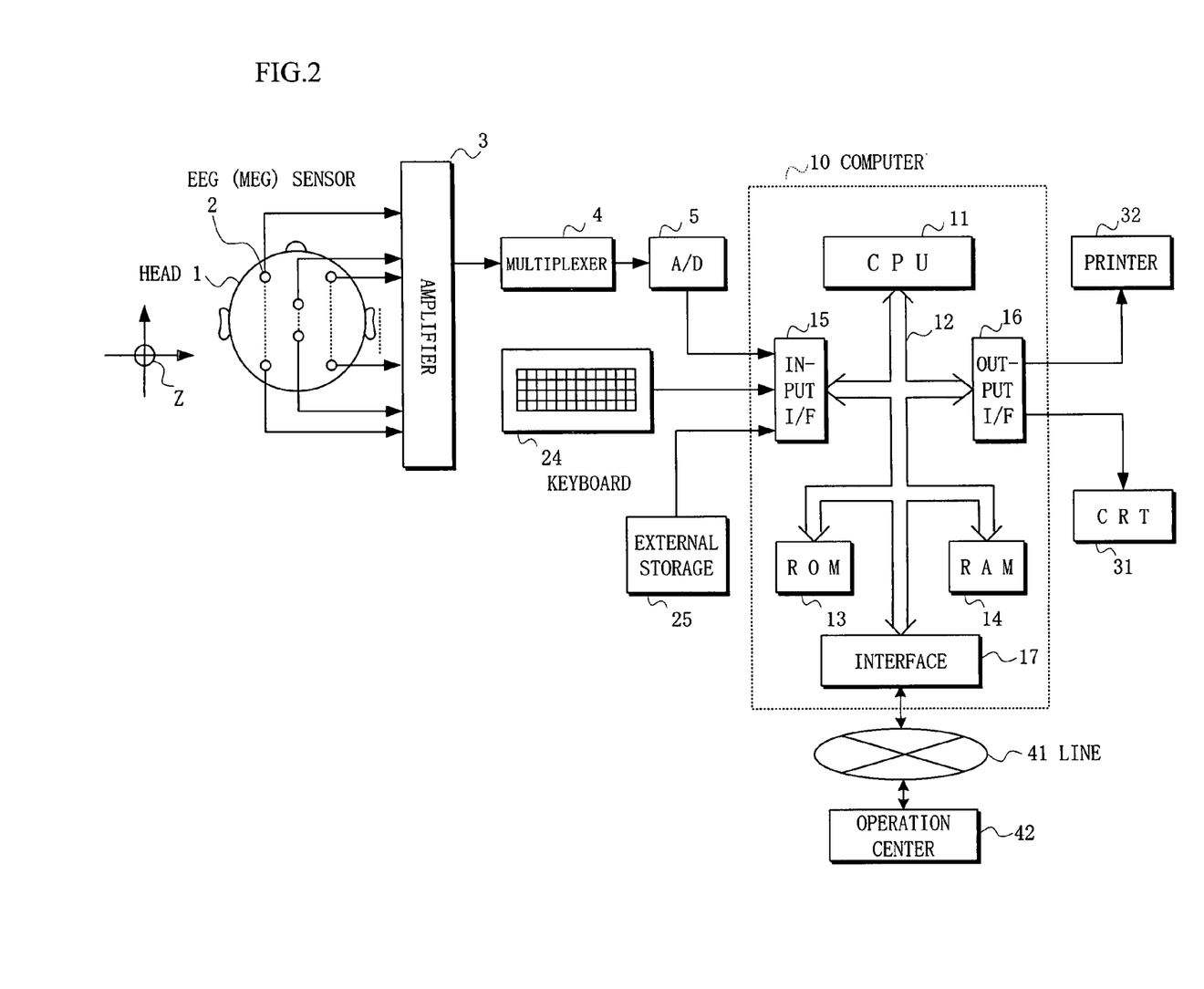
FIG. 2 is a block diagram showing an arrangement [2] of an apparatus for measuring a brain local activity through network according to the present invention.

Arrangement: FIGS. 1 and 2

FIG. 1 shows an arrangement [1] of an apparatus for measuring a brain local activity according to the present invention. In this arrangement, EEG sensors or MEG sensors, which also serve as electrodes, (hereinafter occasionally referred to as sensors) $2_1$-$2_{2i}$ (hereinafter occasionally represented by a reference numeral 2) comprising e.g. 21 sensors are firstly mounted on a head 1 to measure scalp potentials, or a subject puts on a cap or helmet where these sensors are properly arranged. It is to be noted that the sensors 2 in this case are arranged according to the international 10-20 standard, and for a reference potential, another sensor (not shown) is attached to e.g. a right ear lobe.

The scalp potential measured by the sensors 2 is supplied to an analog/digital (A/D) converter 5 through an amplifier 3 and a multiplexer 4, so that digitized measured potential (EEG) data is supplied to a computer 10 through an input interface (I/F) 15. It is to be noted that the input interface 15 may pass the data as it is or after the input interface 15 has taken out only the component having a frequency bandwidth (e.g. predetermined frequency bandwidth wider than e.g. alpha wave) preliminarily designated, by performing digital filtering processing, the data may be outputted.

In the computer 10, a CPU 11 is connected to an ROM 13, an RAM 14, an input interface 15, and an output interface 16 through a bus 12. The above-mentioned ROM 13 is a read only storage medium, and the RAM 14 is a memory for storing EEG data from a keyboard 24 and the A/D converter 5 upon calculation.

Also, an external storage 25 storing programs or the like is connected to the input interface 15. The display 31 of the CRT or the like which displays the operation result of the computer 10 and the printer 32 printing the data and the waveform displayed at the display 31 are connected to the output interface 16 as output units. It is to be noted that all of the programs and the like may be stored only in the ROM 13 without using the external storage 25.

The above-mentioned brain wave data, as shown in an arrangement [2] of FIG. 2, is sent from an interface 17 of the computer 10 in a clinical spot serving as a data transfer terminal equipment to an operation center 42, as a computing (arithmetic) unit through a communication line 41 of the Internet or the like, where the result analyzed at the operation center 42 is again sent back to the computer 10 through the communication line 41, and the result is outputted from an output unit such as a CRT 31 and a printer 32, so that a doctor utilizes the result as the materials for a diagnosis. In this case, the program and the recording medium are provided in the operation center 42.

OPERATION EXAMPLE:

Preparation of Neuronal Abnormality Map and Abnormality Discrimination (FIGS. 3-7)

Figure 3:
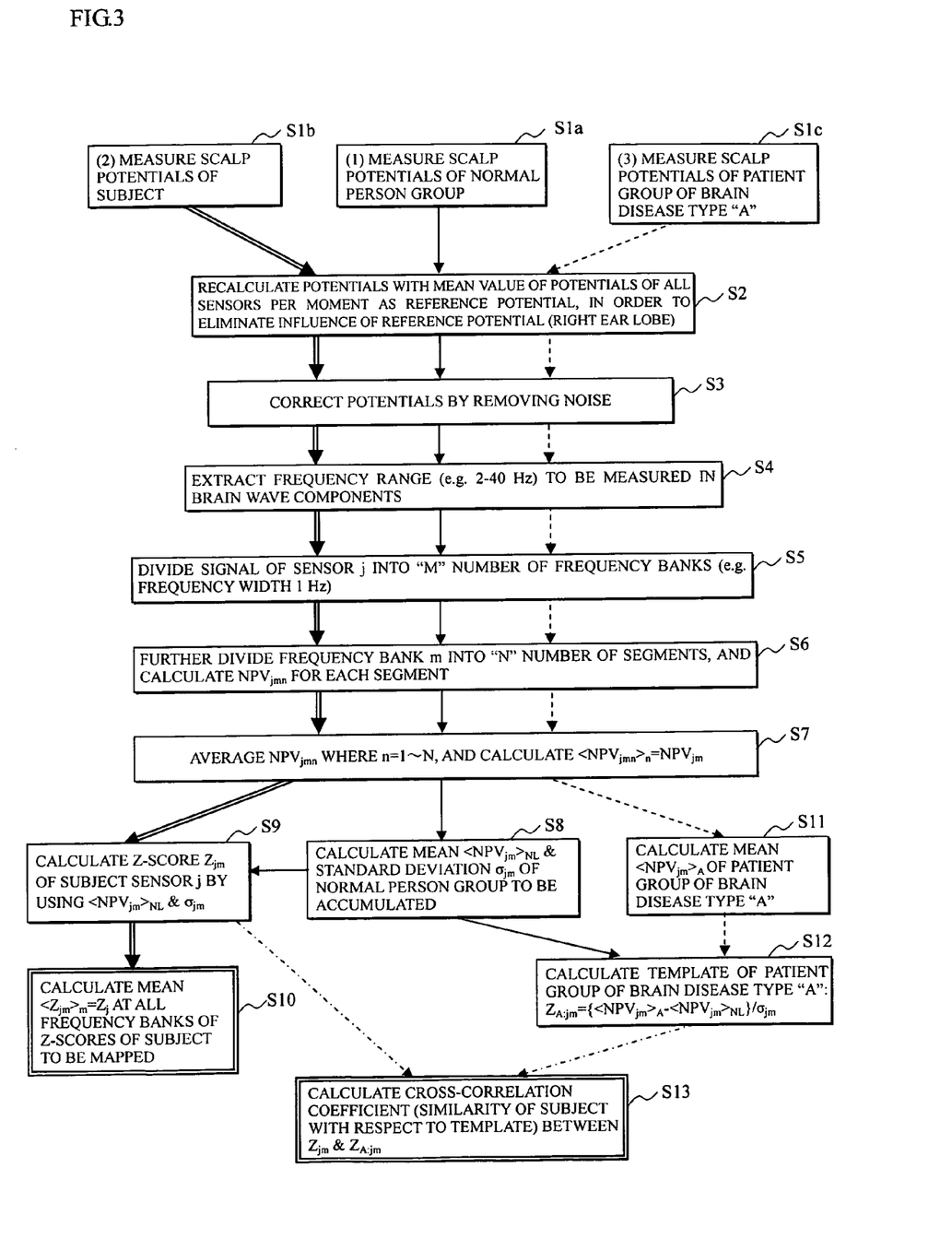
FIG. 3 is a flowchart showing a processing procedure of an apparatus for measuring a brain local activity according to the present invention and calculating template of a specified brain disorder and likelihood of a subject to a specified brain disorder.
Figure 4:
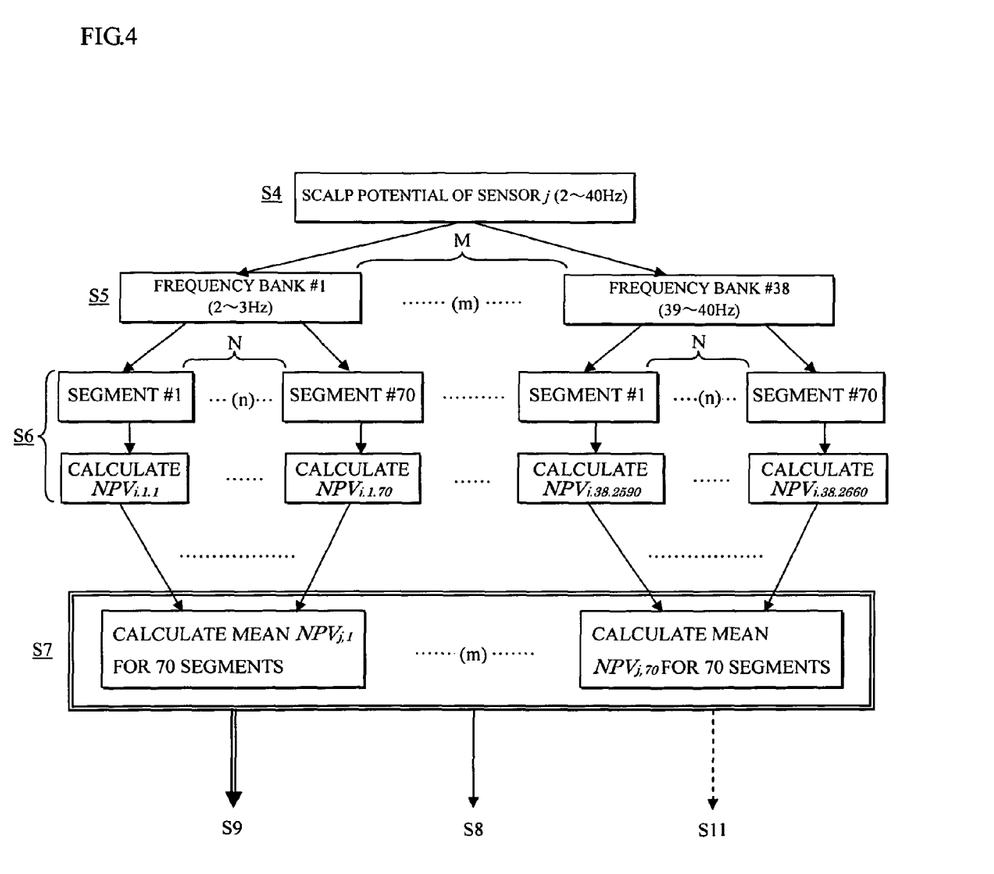
FIG. 4 is a flowchart more intelligibly showing a processing part common to a subject, a normal person group, and a group of (a) brain disease patients in the flowchart shown in FIG. 3.

The operation example of the above-mentioned arrangements will now be described along the flowcharts of FIG. 3 and FIG. 4 which specifically shows a portion (processing part common to a subject, a normal person group and a group of brain disease patients (a group of persons in brain disorder) of FIG. 3. It is to be noted that after the sensor group 2 is arranged on the head 1, the computer 10 is initialized upon power-up. Also, measuring the scalp potential based on the brain neuronal activity is performed at a fixed sampling time interval with the 21 sensors $2_1$-$2_{21}$ mounted on the head 1.

(1) Preparation of Database (NPV+σ) of Normal Person Group (Along Processing Route Shown by Solid Line Arrow)

Step S1a:

Firstly, a normal person group among a fixed number of persons is predetermined by the existing Mini-Mental State Examination (MMSE) method, the SPECT (Single Photon Emission Computing Tomography), or the like, and the scalp potentials on the head are measured one by one.

Step S2:

In this case, the potential (voltage) signals of the sensors j (j=1-21) are recorded with the right ear lobe or the like as a reference potential, so that in order to eliminate this influence the mean value of all of the sensor potentials is recalculated as a reference potential.

Step S3:

The potentials are corrected for noises such as a body motion, myoelectric potential, and amplifier saturation.

Step S4:

By bandpass filtering, signals within a fixed frequency bandwidth (e.g. 2-40 Hz) wider than the frequency bandwidth of the alpha waves are extracted.

Step S5:

A time series of signals from the sensor (channel) "j" is divided into M (m=1-38) number of frequency banks (bandwidths) on a frequency axis. In this case, M=38 and the frequency bandwidth is 1 Hz.

Step S6:

Each frequency bank represented by "m" is further divided into N (n=1-70) number of segments on a time axis, and a Normalized Power Variance $NPV_{jmn}$ is calculated for each segment represented by "n".

This $NPV_{jmn}$ is expressed by the following equation with a signal voltage being made "x":

$$NPV_{jmn} = <x^4>/<x^2>^2 - 1 \qquad \text{Eq. (1)}$$

where $< \ldots >$ represents a time mean within the segment "n".

More specifically, the following equation can be obtained:

$$NPV_m = <<<x_{j,m}^4>_n/<x_{j,m}^2>_n^2>_{over\,j}>_{over\,n} - 1 \qquad \text{Eq. (2)}$$

Step S7:

A mean value $<NPV_{jmn}>_{in\,n}$ of normalized power variances $NPV_{jmn}$ determined over all of the segments n=1-N is stored in the RAM 14 as a normalized power variance $NPV_{jm}$ when the sensor "j" and the frequency bank "m" are designated.

Step S8:

By repeating the above-mentioned steps S1a-S7 with respect to all of the normal persons, a group mean $<NPV_{jm}>_{NL}$ in the normal person group and a standard deviation $\sigma_{jm}$ within the group are calculated, so that the results are stored in the RAM 14 as a database.

(2) Preparation of Subject's Z-Score Map (Along Processing Route Shown by Double Solid Line Arrow)

Step S1b:

The scalp potentials from the sensor 2 attached on the subject are measured.

Steps S2-S7:

Steps S2-S7 are repeatedly executed in the same manner as the case of the above-mentioned normal person group, so that the normalized power variance $NPV_{jm}$ of the subject is calculated.

Step S9:

The Z-score of the subject is determined based on the normalized power variance $NPV_{jm}$ of the subject, the mean normalized power variance $<NPV_{jm}>_{NL}$ and the standard deviation $\sigma_{jm}$ of the normal person group by the following equation:

$$z_{jm} = \frac{NPV_{jm} - <NPV_{jm}>_{NL}}{\sigma_{jm}} \qquad \text{Eq. (3)}$$

Step S10:

By averaging this $Z_{jm}$ for all of the frequency banks M, a function $Z_j$ only for the sensor "j" is obtained, which assumes the mean value of the Z-score of the sensor "j" on the subject. This is determined for all of the sensors to be mapped.

Figure 5:
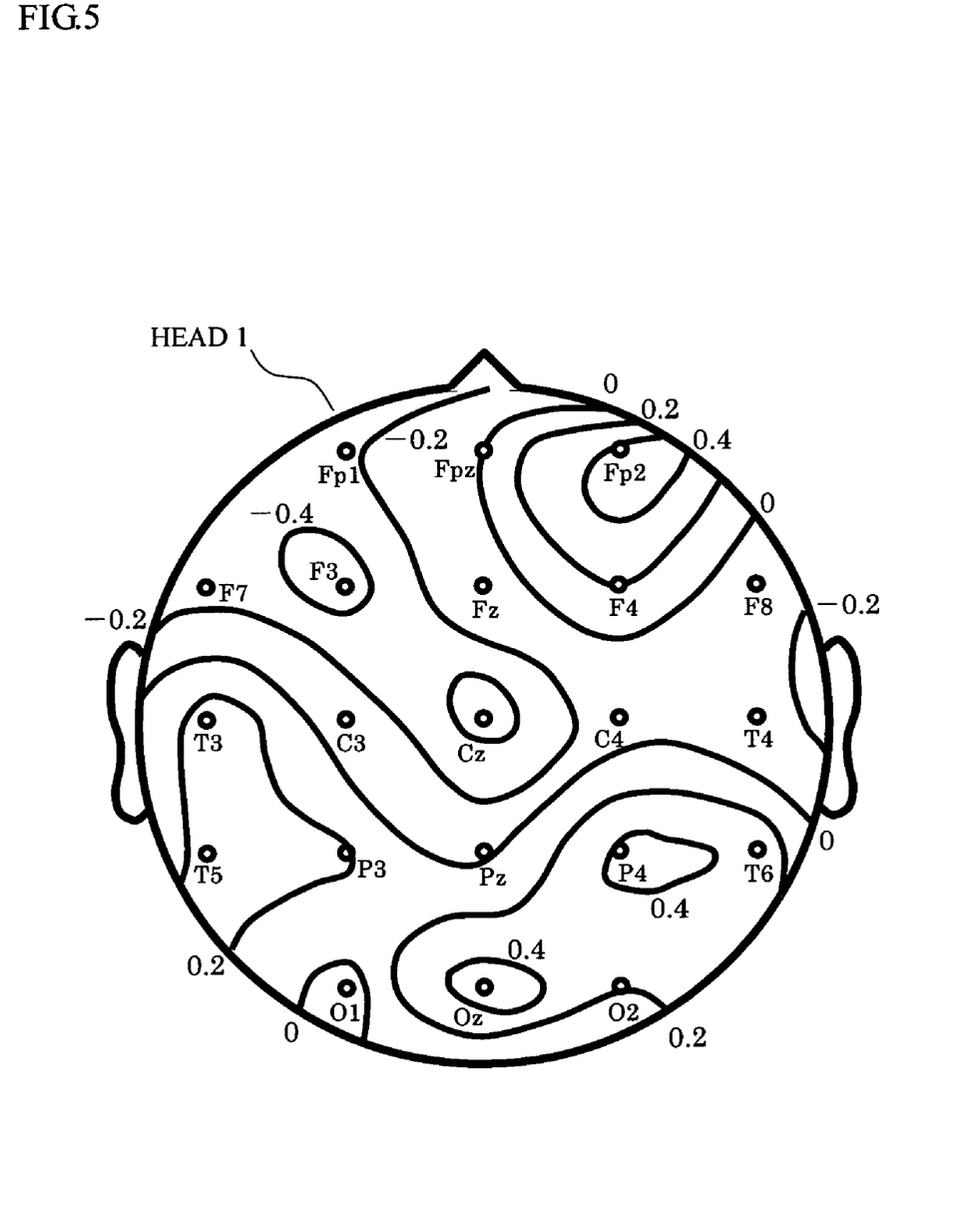
FIG. 5 is a diagram exemplifying a map of Z-score mean values determined by an apparatus for measuring a brain local activity according to the present invention.

FIG. 5 shows a Z-score mean value map thus prepared of the head 1 of a certain subject. This Z-score mean value map shows plus numbers and minus numbers, in which the Z-score mean value assumes a minus value when the normalized power variance $NPV_j$ assumes a value smaller than the mean value $<NPV_j>_{NL}$ with respect to the sensor "j" of the normal person group. Namely, it means that the power fluctuation of the sensor "j" of the subject is smaller than the power fluctuation of the sensor "j" corresponding to the normal person, indicating such an abnormality that the neuronal activity is inactive compared with the normal person.

Contrarily, the plus value of the Z-score mean value shows the abnormality when the fluctuation of the neuronal activity is larger than that of the normal person group so that the neuronal activity is "unstable". The larger the absolute value is, the larger the abnormality is.

(3) Preparation of Database (Template) of a Patient Group of a Brain Disease Type a (Along Processing Route Shown by Dotted Line Arrow)

Step S1c:

In the same way as the above-mentioned case of the normal person group, the patient group with the brain disease type A is specified by the MMSE method, the SPECT, or the like, and the scalp potentials on the head from the sensor 2 are measured one by one.

Steps S2-S7:

In the same way as the above-mentioned case of the normal person group or the subject, steps S2-S7 are repeatedly executed, so that a normalized power variance $NPV_{jm}$ of the patient of the brain disease type A is calculated.

Step S11:

$<NPV_{jm}>_A$ is determined by averaging the normalized power variances $NPV_{jm}$ in the patient group of the brain disease type A.

Step S12:

A template of the Z-score of the patient group of the brain disease type A is calculated by using $<NPV_{jm}>_{NL}$ and $\sigma_{jm}$ of the normal person group as expressed by the following equation:

$$Z_{A;jm} \equiv \frac{<NPV_{jm}>_A - <NPV_{jm}>_{NL}}{\sigma_{jm}} \qquad \text{Eq. (4)}$$

Step S13:

The cross-correlation coefficient between $Z_{jm}$ of the subject determined at step S9 and the template $Z_{A;jm}$ of the patient of the brain disease type A determined at step S12 is calculated by the following equation:

$$\text{Cross-correlation coefficient} = \frac{<Z_{jm} Z_{A;jm}>_{jm}}{\sqrt{<Z_{jm}^2>_{jm} <Z_{A;jm}^2>_{jm}}} \qquad \text{Eq. (5)}$$

Figure 6A:
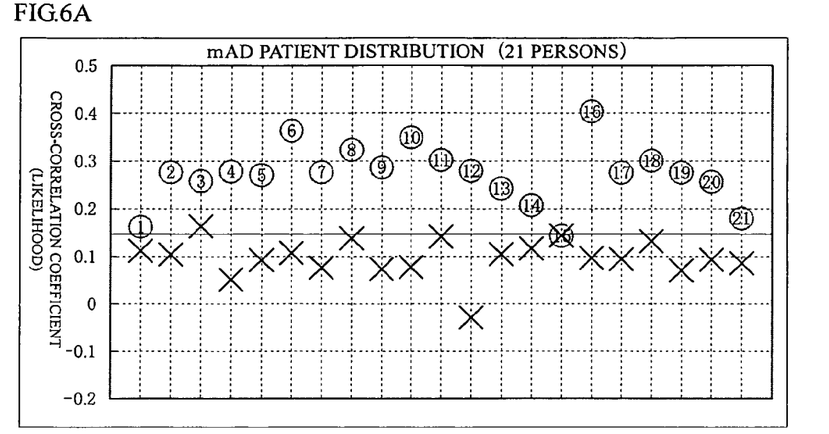
FIGS. 6A-6C are graphs showing a cross-correlation coefficient (likelihood) per subject of an apparatus for measuring a brain local activity according to the present invention.
Figure 6B:
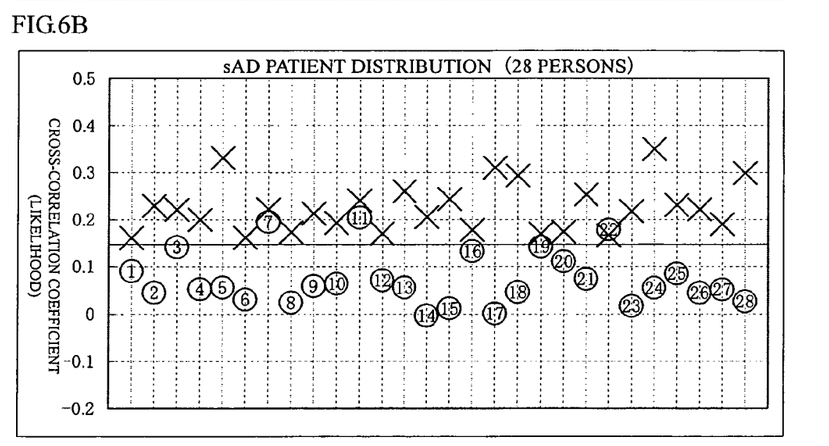
Figure 6C:
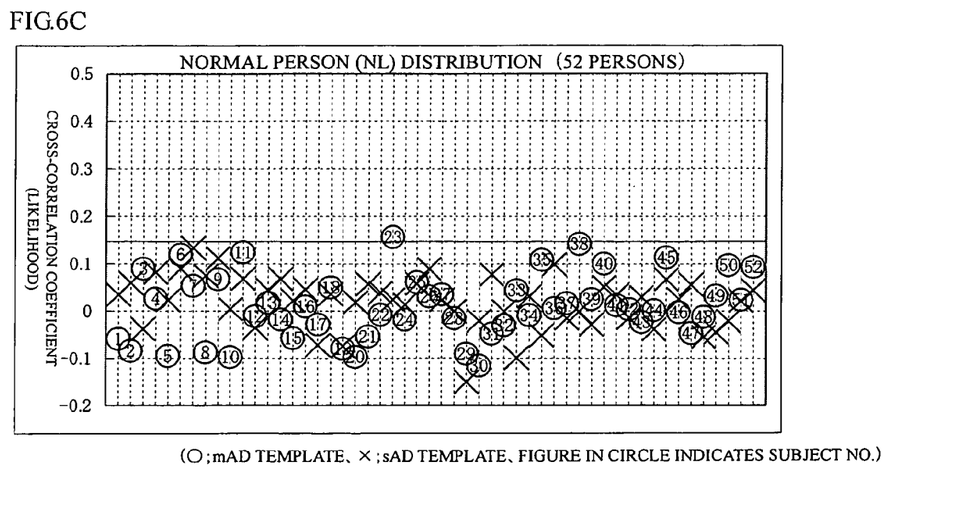

FIGS. 6A-6C show the cross-correlation coefficients determined for three groups of the normal person group (NL) (including 52 persons), m (mild) AD (brain disease person with a comparatively mild symptom) (including 21 persons), and s (moderately severe) AD (brain disease person with a comparatively severe symptom) (including 28 persons) with respect to two types of templates of mAD and sAD. It is to be noted that a figure in a circle of FIGS. 6A-6C indicates a subject No., and that the mark X at the same abscissa position indicates the cross-correlation coefficient of the same subject.

FIG. 6A shows the cross-correlation coefficients between 21 mild AD patients, the template of the mild AD (mark ○), and the template of the moderately severe AD (mark X). When the subject is mild AD, the combination with the mild AD template indicates the high cross-correlation coefficients and a high likelihood as expected. For the moderately severe AD template, the cross-correlation coefficients become small, so that it is recognized that they are distinguished from each other.

FIG. 6B shows a case where the same two templates are applied to the moderately severe AD subject group of 28 persons, so that it is recognized that they are also distinguished from each other.

FIG. 6C shows a case where the same two templates are applied to the normal subject group of 52 persons, and that the cross-correlation coefficients are low and the likelihood is low for either template.

Figure 7:
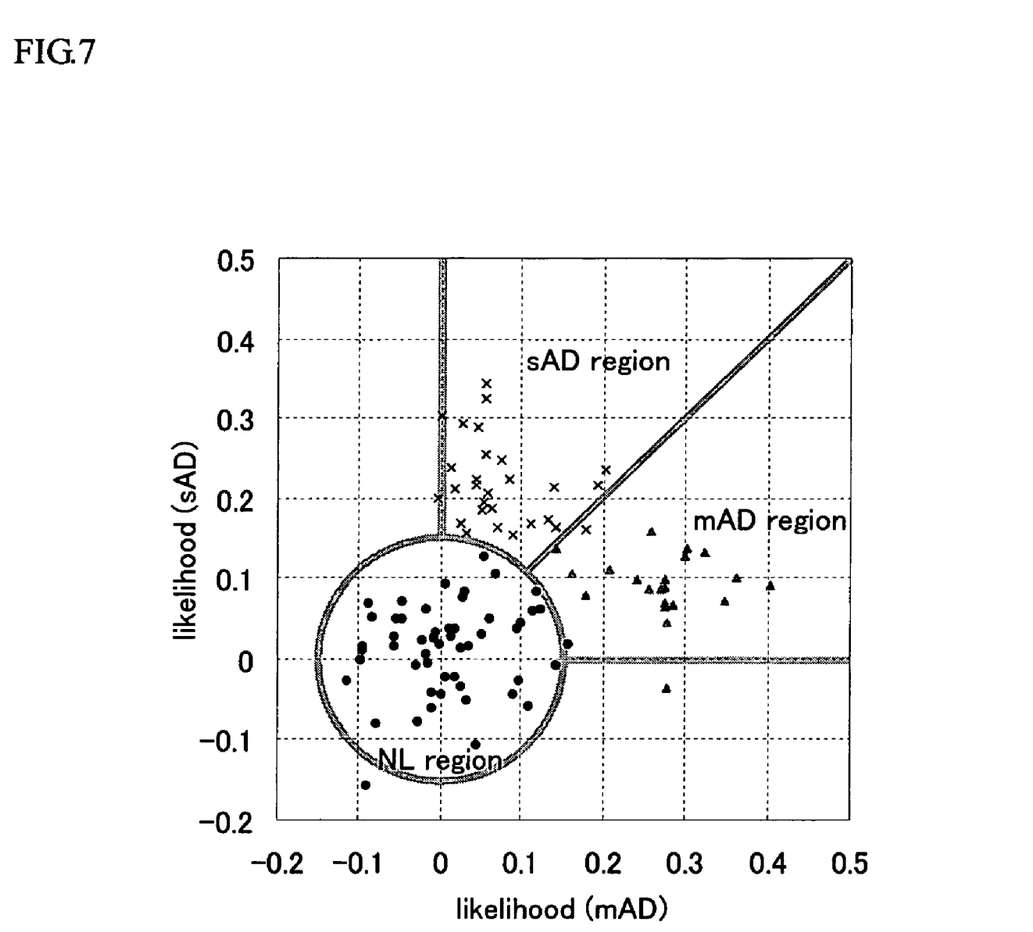
FIG. 7 is a graph modifying the graphs of FIGS. 6A-6C.

FIG. 7 shows a likelihood diagram modifying FIGS. 6A-6C, where patients in moderately severe Alzheimer's disease (sAD) and mild Alzheimer's Disease are distributed separately in two different sectors and normal persons (NL) are distributed within a circle of radius 1.5 with its center on the origin of the coordinate system. Here the ordinate is likelihood with sAD and the abscissa is likelihood with mAD.

It is to be noted that the present invention is not limited by the above-mentioned embodiments, and it is obvious that various modifications may be made by one skilled in the art based on the recitation of the claims.

What is claimed is:

1. An apparatus for measuring a brain local activity comprising:
   a plurality of sensors mounted on a head of a subject for measuring scalp potentials of the subject; and
   a computing unit dividing, for each sensor, a predetermined frequency bandwidth wider than a frequency bandwidth of alpha waves of the scalp potentials outputted from the sensors into a predetermined number of frequency banks each having a fixed frequency bandwidth, dividing, for each sensor, data of each divided frequency bank into segments of a predetermined duration on a time axis, determining, for each sensor, a Z-score of the subject from a first mean value, for each frequency bank, of normalized power variances determined for the segments and a second mean value, for each frequency bank, of normalized power variances predetermined in the same manner as the first mean value for a predetermined normal person group and a standard deviation of the normalized power variances in the group, and mapping on a brain surface for each sensor a mean value of the Z-scores determined over all of the frequency banks.

2. The apparatus for measuring a brain local activity as claimed in claim 1, wherein the computing unit further determines mean values of the Z-scores, for each sensor, over a patient group of a specific brain disease with respect to the predetermined normal person group, and determines cross-correlation coefficients as a likelihood to the Z-scores, for all of the sensors, of the subject with means values of the Z-scores, for all of the sensors, over the patient group being made a template.

3. The apparatus for measuring a brain local activity as claimed in claim 1, wherein the predetermined frequency bandwidth is 2-40 Hz, the fixed frequency bandwidth is 1 Hz, the predetermined number is 38, and the predetermined duration is 2.56 seconds.

4. The apparatus for measuring a brain local activity as claimed in claim 1, wherein the sensors are set in a terminal device, the computing unit is provided in a calculation center, and the terminal device and the calculation center are connected through a communication line.

5. A computer-readable medium encoded with a computer program for measuring a brain local activity, the program when executed by a computer causes the computer to perform a method comprising:
   measuring scalp potentials of a subject from a plurality of sensors mounted on a head of the subject; and
   dividing, for each sensor, a predetermined frequency bandwidth wider than a frequency bandwidth of alpha waves of the scalp potentials measured by a plurality of sensors mounted on a head of a subject into a predetermined number of frequency banks each having a fixed frequency bandwidth, dividing, for each sensor, data of each divided frequency bank into segments of a predetermined duration on a time axis, determining, for each sensor, a Z-score of the subject from a first mean value, for each frequency bank, of normalized power variances determined for the segments and a second mean value, for each frequency bank, of normalized power variances predetermined in the same manner as the first mean value for a predetermined normal person group and a standard deviation of the normalized power variances in the group, and mapping on a brain surface for each sensor a mean value of the Z-scores determined over all of the frequency banks.

6. The computer-readable medium as claimed in claim 5, wherein the program when executed by a computer causes the computer to further perform:
   determining mean values of the Z-scores, for each sensor, over a patient group of a specific brain disease with respect to the predetermined normal person group, and determining cross-correlation coefficients as a likelihood to the Z-scores, for all of the sensors, of the subject with mean values of the Z-scores, for all of the sensors, over the patient group being made a template.

* * * * *